United States Patent [19]

Kitahara et al.

[11] Patent Number: 5,525,335
[45] Date of Patent: Jun. 11, 1996

[54] WOUND HEALING AGENT

[75] Inventors: Yoshiro Kitahara, Kawasaki; Tsuyoshi Ohsumi, Tokyo; Yuzuru Eto; Satoshi Takano, both of Kawasaki, all of Japan

[73] Assignee: Ajinomoto Co., Inc., Tokyo, Japan

[21] Appl. No.: 167,806

[22] PCT Filed: Apr. 19, 1993

[86] PCT No.: PCT/JP93/00501

§ 371 Date: Dec. 21, 1993

§ 102(e) Date: Dec. 21, 1993

[87] PCT Pub. No.: WO93/20837

PCT Pub. Date: Oct. 28, 1993

[30] Foreign Application Priority Data

Apr. 21, 1992 [JP] Japan ................................. 4-101184

[51] Int. Cl.⁶ ..................................................... A61K 38/45
[52] U.S. Cl. ............................................. 424/94.5; 435/193
[58] Field of Search ............................. 424/94.5; 435/193

[56] References Cited

U.S. PATENT DOCUMENTS 5,156,956  10/1992  Motoki et al. ................. 435/68.1

FOREIGN PATENT DOCUMENTS

| | | |
|---|---|---|
| 4090489 | 3/1990 | Australia . |
| 0162426 | 11/1985 | European Pat. Off. . |
| 0172710 | 2/1986 | European Pat. Off. . |
| 0330049 | 8/1989 | European Pat. Off. . |
| 0379606 | 8/1990 | European Pat. Off. . |
| 03095109 | 4/1991 | Japan . |
| WO-A-89 01512 | 2/1989 | WIPO . |
| 8901512 | 2/1989 | WIPO . |
| WO-A-92 12238 | 7/1992 | WIPO . |
| WO-A-93 13207 | 7/1993 | WIPO . |
| WO-A-93 12813 | 7/1993 | WIPO . |

OTHER PUBLICATIONS

Bum Suk Tchai et al., "Role of Tissue Transglutaminase in Scar Formation and Graft Versus Host Reaction", *Chemical Abstracts*, 227848, vol. 109, No. 25, Dec. 19, 1988.

J. Michael Bowness et al., "Increased Transglutaminase Activity During Skin Wound Healing in Rats", *Biochimica et Biophysica Acta*, 1988, vol. 967, No. 2, pp. 234–240.

E. Cocuzzi et al., "Transglutaminase Expression in Rat Parotid Gland After Isoproterenol Stimulation", *Journal of Dental Research*, Nov. 1989, vol. 68, No. 11.

*Primary Examiner*—Michael G. Wityshyn
*Assistant Examiner*—Jean C. Witz
*Attorney, Agent, or Firm*—Oblon, Spivak, McClelland, Maier & Neustadt

[57] ABSTRACT

Wound healing agents (especially a cicatricial contracture preventing agent, a wound protective or coating agent and a hemostatic agent) containing transglutaminase as an active ingredient, which are novel and excellent wound healing agents with which cicatricial contracture prevention, wound protection or coating and blood stanching can be made simply and easily.

8 Claims, 1 Drawing Sheet

WOUND HEALING AGENT

TECHNICAL FIELD

This invention relates to a wound healing agent, a cicatricial contracture preventing agent, a wound protective or coating agent and a hemostatic agent, each of which contains transglutaminase as an active ingredient.

BACKGROUND ART

The following facts are known with regard to the medical care-related use of transglutaminase. Firstly, Japanese Patent Application Laid-Open (Kokai) No. Sho 62-74360 discloses an artificial skin which contains as a component a membrane made of crosslinked protein and/or peptide with action of transglutaminase, and this artificial skin is possessed of high biological compatibility, because not only it is excellent in its tensile strength, elongation, flexibility and oxygen permeability but also it has excellent water vapor permeability. Also, Japanese Patent Application Laid-Open (Kokai) No. Hei 2-108631 discloses an immunosuppressive agent which contains transglutaminase as the active ingredient, but the disclosure is limited to in vitro experiments and immunological discussions and is not even suggestive of actual wound healing in vivo. In addition, as will be described later, such use of transglutaminase is evidently different from that of the present invention.

As for wound healing, post-disinfection primary suture and the like treatments are generally carried out, which essentially require surgical operation. However, it is difficult to apply surgical suture to a wound having large skin damage, as well as burn injury and the like.

On the other hand, it is extremely important in the case of wound healing to treat the wound without leaving a scar behind, not only from organic and functional points of view but also from a cosmetic point of view.

Skin grafting, redressing appliance application, pharmacotherapy, radiotherapy and the like are generally employed in order to prevent such a cicatricial contracture, but each means has its own drawbacks. That is, in the case of skin grafting, several problems have been pointed out which include not only a necessity of carrying out surgical treatments, but also a difficulty in carrying out ideal skin grafting when a wound covers a wide area like in the case of heavy burn injury because of extreme limitation in obtaining the donor skin, and a wound contraction which does not stop immediately after the skin grafting but continues for a considerably prolonged period of time on the interface between the grafted skin and the wound surface, the skin graft suture line and the like. As to the use of a redressing appliance, notwithstanding such use is an auxiliary means and such appliance needs a long-time application accordingly, some problems have been pointed out in that such appliance cannot actually be used for a prolonged period of time required for the treatment. With regard to pharmacotherapy, distinct effects cannot be expected from steroid ointments, and only an auxiliary effect can be expected from tranilast which has a function to inhibit degranulation of mast cells. Though radiotherapy can repress wound contraction, it has a drawback in that it inhibits healing of wounds.

Several wound protectives have also been proposed and put into practical use, but each has its own problems. That is, in the case of a lyophilized porcine skin, re-covering is required because such a skin melts on the wound surface, and it also requires regeneration with physiological saline prior to its use. An artificial skin made of collagen sometimes causes a slight pain and an uncomfortable feeling. A plasma membrane and a fibrin membrane made from human blood are not capable of fully discharging exudate when the wound surface is secretory, and the supply of these membranes is limited because of the use of human blood as a raw material. In addition, pains and uncomfortable feelings at the time of application are commonly seen in all these wound protectives. What is more, all these wound protectives are not sufficiently possessed of functions necessary for the treatment process, in terms of drying of the affected part, stanching of blood, prevention of infection and the like.

As hemostatic agents, gelatin, fine fibrous collagen, thrombin and the like are indeed known, but with increasing demand for the development of more excellent agents.

DISCLOSURE OF THE INVENTION

The applicants of the present invention have made intensive efforts to develop production processes of transglutaminase and to find versatile use thereof, with a number of patent applications already filed for based on the results. Under the background of such efforts and in view of the aforementioned situation involved in the prior art, it is one of the objects of the present invention to provide a novel wound healing agent which contains transglutaminase as an active ingredient, thus rendering possible opening of a new field of the use of this enzyme.

As a result of intensive studies with a view to achieving the aforementioned objects, the inventors of the present invention have found that transglutaminase has a broad range of wound healing functions which include a cicatricial contracture preventing function and a wound protecting function that exerts pain suppressing, affected part drying, blood stanching and the like effects, and have accomplished the present invention on the basis of these findings. Briefly adding a remark about hemostatic functions, the hemostatic effect of transglutaminase may be utilized not only in the case of wound protection but also, e.g., in the field of surgery and in the emergency treatment of wounds caused by an accident.

Accordingly, the present invention relates to a wound healing agent, a cicatricial contracture preventing agent, a wound protective preparation and a hemostatic agent, each of which contains transglutaminase as an active ingredient.

Hereinbelow, the present invention will be explained in detail.

Transglutaminase to be used as an active ingredient of the wound healing agent of the present invention can be classified into calcium-independent and calcium-dependent types. Examples of the former type include those of microbial origin (see, for instance, Japanese Patent Application Laid-Open (Kokai) No. Sho 64-27471), and examples of the latter type include those of guinea pig origin (see, for instance, Japanese Patent Publication (Kokoku) No. Hei 1-50382), fish origin (see, for example, N. Seki et al. "Abstract of Papers, 1988 Autumn Meeting of the Japanese Society of Scientific Fisheries", page 167, and "Abstract of Papers, 1990 Spring Meeting of the Japanese Society of Scientific Fisheries", page 219), and human origin (factor XIII (fibrin stabilizing factor), for instance). Of these, the calcium-independent type is preferable, which can be produced in accordance with the procedure disclosed in the aforementioned Japanese Patent Application Laid-Open (Kokai) No. Sho 64-27471.

Examples of the dosage form of the transglutaminase-containing wound healing agent of the present invention include transglutaminase itself, solutions containing the same, and other administration forms suitable for topical application in which semi-liquid fillers or auxiliaries are used, out of which solutions, ointments, topical protectives such as absorbent gauze soaked with transglutaminase, sprays and the like are preferred from the application point of view. Solutions can be prepared by dissolving transglutaminase in solvents such as sterile water, various types of buffer solutions and the like. As to ointments, their base materials are not particularly limited and can be selected optionally from usually used materials such as fats, fatty oils, lanolin, petrolatum, paraffin, wax, plaster bases, resins, plastics, glycols, higher alcohols, glycerol, water, emulsifying agents, suspending agents and the like. Such solutions, ointments, topical protectives, sprays and the like, though not particularly limited in their transglutaminase content, may contain transglutaminase in an amount of from approximately 0.1 to 1,000 U/g, preferably from approximately 0.5 to 500 U/g, for convenience' sake of administration.

The wound healing agent of the present invention may be applied onto wounds by dusting, spraying, spreading, wet compressing and the like means.

When the wound healing agent of the present invention is used as a cicatricial contracture preventing agent, the wounds to be treated include, for example, burn injuries, other injuries caused by a surgical operation and the like wounds.

When it is used as wound protectives, the wounds to be treated include, in addition to the above-mentioned wounds, diabetic angiopathy, chronic skin ulcer, post-thrombosis ulcer, decubital ulcer and the like. The wound protective or coating preparation or agent of the present invention has a wound infection preventing function, a wound analgesic function, an affected part drying function and the like. Incidentally, among commonly known infection prevention treatments, sanitization of wounds with a disinfectant or the like is merely a temporary treatment, and the use of antibacterial agents is dogged by a possible danger of infection with drug-resistant microbial strains. In addition, protection of wounds with wound protectives or the like used in the prior-art requires fixation for their adhesion, as well as other problems such as pains, uncomfortable feelings, discharge of secretory fluid and the like during their use and at the time of their attachment or removal.

When it is used as a hemostatic agent, the inventive agent is effective in stanching various types of bleeding in the surgical field and the like.

The wound healing agent of the present invention can exert its therapeutic effects upon other broad range of wounds.

According to the wound healing agent of the present invention, prevention of cicatricial contracture, protection or coating of wounds and stanching of blood can be made markedly easily.

As a matter of course, the wound healing agent of the present invention can be used for the treatment of wounds of not only human but also other animals.

BEST MODE OF CARRYING OUT THE INVENTION

Figure 1:
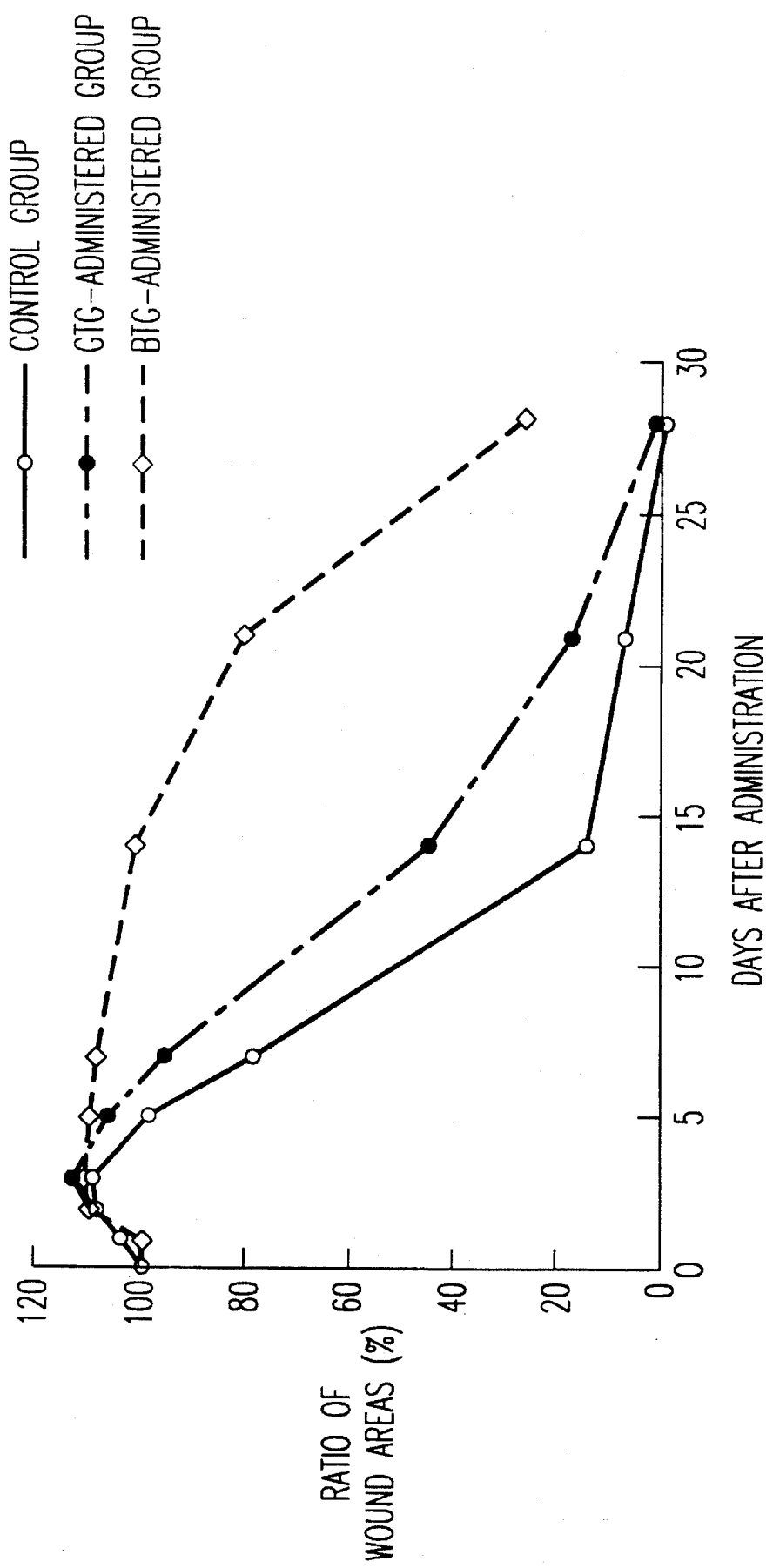
FIG. 1 is a graph showing experimental results obtained in Example 2 (changes in the wound area).

The following examples are provided to further illustrate the present invention.

Example 1 (Preparation of therapeutic agent)

(a) Preparation of transglutaminase solution (1)

Microbial transglutaminase (BTG) was prepared in accordance with the procedure of Example 1 disclosed in Japanese Patent Application Laid-Open (Kokai) Sho No. 64-27471 (specific activity, 3 U/mg).

A 5 g portion of the thus prepared transglutaminase was dissolved in 100 ml of 50 mM HEPES buffer (pH 7) to obtain a wound healing agent (a 5% (w/v) aqueous solution of microbial transglutaminase).

(b) Preparation of transglutaminase solution (2)

A 5 g portion of guinea pig transglutaminase (GTG) prepared in accordance with the procedure disclosed in the aforementioned Japanese Patent Publication (Kokoku) No. Hei 1-50382 (specific activity, 3 U/mg) was dissolved in 100 ml of 50 mM HEPES buffer (pH 7) to prepare a wound healing agent (a 5% (w/v) aqueous solution of guinea pig transglutaminase).

Example 2 (Cicatrical contracture preventing effect)

30 seven-week-old male rats of the SD line were divided into 3 groups, each of which included 10 animals.

Under anesthesia, each rat was sheared (about 7 cm×7 cm) at its dorsal portion, and the sheared part was disinfected with a "Hibitane" solution, from which part a piece of the skin (epidermis+dermis) was subsequently excised in a size of about 5 cm square using a scalpel. After measuring the area of the resulting wound, a piece of absorbent gauze soaked in the transglutaminase solution (1) prepared in Example 1 (a) was applied to the wound of each rat of a first group (Group I), a piece of absorbent gauze soaked in the transglutaminase solution (2) prepared in Example 1 (b) was applied to the wound of each rat of a second group (Group II) and a piece of absorbent gauze soaked in a 50 mM HEPES buffer (pH 7) was applied to the wound of each rat of a third group (Group III, the control group), and each gauze was fixed with a bandage.

Thereafter, changes in the wound were observed every day by measuring the wound area, and administering fresh transglutaminase solutions and HEPES buffer in the aforementioned manner with the gauze fixed with a bandage.

Changes in the ratio of wound areas in this test (ratio of the area on each observation day to the area on the first day of the test) are shown in FIG. 1. As is evident from the figure, transglutaminase has a cicatricial contracture preventing effect.

Example 3 (Wound protecting or coating effect)

20 seven-week-old male rats of the SD line were divided into 2 groups, each of which included 10 animals.

In the same manner as described in Example 2, each rat was sheared (about 7 cm×7 cm) at its dorsal portion under anesthesia, and the sheared part was disinfected with a "Hibitane" solution, from which part a piece of the skin (epidermis+dermis) was subsequently excised in a size of about 5 cm square using a scalpel. A piece of absorbent gauze soaked in the transglutaminase solution (1) prepared in Example 1 (a) was applied to the wound of each rat of one group (Group I) and a piece of absorbent gauze soaked in a 50 mM HEPES buffer (pH 7) was applied to the wound of each rat of the other group (Group III, a control group), each application being followed by fixing of each gauze with a bandage.

Thereafter, changes in the wound were observed every day by observing the wound conditions, and administering fresh transglutaminase solutions and HEPES buffer in the aforementioned manner with the gauze fixed with a bandage.

Findings obtained by the daily observation of the wound in this test are shown in Table 1. As is evident from the table, transglutaminase has a clinically excellent wound protecting or coating effect.

(d) Administration and test methods:

After 4 hours of the wound making on the day of the wound provision, the transglutaminase test solution, the blood coagulation factor XIII test solution and the blank test solution were respectively administered to rats of Groups I to III. That is, the wound portion of each rat was covered with a piece of absorbent gauze which had been cut into such a size that it completely covered the entire wound, and each test solution was added dropwise to the entire wound area at a dose of 1 ml per animal using a syringe. The administration

TABLE 1

| | Findings from daily observation of wounds | | | | | | | | | | | | | |
|---|---|---|---|---|---|---|---|---|---|---|---|---|---|---|
| | Days after administration (days) | | | | | | | | | | | | | |
| Wound protective effects (findings) | 1 | 2 | 3 | 4 | 5 | 6 | 7 | 8 | 9 | 10 | 11 | 12 | 13 | 14 |
| Control group | | | | | | | | | | | | | | |
| Dry wound surface | 0 | 0 | 0 | 0 | 0 | 0 | 0 | 0 | 0 | 0 | 0 | 0 | 0 | 0 |
| No bleeding | 0 | 0 | 0 | 0 | 0 | 0 | 0 | 0 | 0 | 0 | 50 | 70 | 100 | 100 |
| No complaint of pain when the gauze was removed (no squeak) | 0 | 0 | 0 | 0 | 0 | 0 | 60 | 50 | 70 | 80 | 100 | 100 | 100 | 100 |
| Fusion of wound periphery with subcutaneous tissue | 0 | 0 | 60 | 100 | 100 | 100 | 100 | 100 | 100 | 100 | 100 | 100 | 100 | 100 |
| TG administrated group | | | | | | | | | | | | | | |
| Dry wound surface | 0 | 80 | 100 | 100 | 100 | 100 | 100 | 100 | 100 | 100 | 100 | 100 | 100 | 100 |
| No bleeding | 70 | 100 | 100 | 100 | 100 | 100 | 100 | 100 | 100 | 100 | 100 | 100 | 100 | 100 |
| No complaint of pain when the gauze was removed (no squeak) | 90 | 100 | 100 | 100 | 100 | 100 | 100 | 100 | 100 | 100 | 100 | 100 | 100 | 100 |
| Fusion of wound periphery with subcutaneous tissue | 0 | 0 | 50 | 70 | 100 | 100 | 100 | 100 | 100 | 100 | 100 | 100 | 100 | 100 |

As for each test group, the ratio of the number of rats fitted to the finding of each observation item to the total number of rats used in the test was expressed by percentage (%).

Example 4 (Blood stanching effect)

(a) Experimental animals:

15 seven-week-old male rats of the SD line were divided into 3 groups, each of which included 5 animals. Using these 3 groups, a text on the hemostatic agent of the present invention (Inventive example), another text on blood coagulation factor XIII (Comparative example) and a blank test (Control example) were carried out.

(b) Materials tested and preparation thereof:

Transglutaminase (specific activity, 3 U/mg) prepared in the same manner as described in Example 1 (a) was purified in accordance with the procedure of Hiroyasu Ando et al. (Agric. Biol. Chem., 53, 2613 (1989)) to obtain a 30 U/ml solution of transglutaminase. This was dissolved in a 50 mM HEPES buffer (pH 7) to prepare a test solution having a concentration of 3 U/ml (Inventive example).

The same procedure was repeated except that a preparation of blood coagulation factor XIII, "Fibrogammin P" (ex Hoechst Japan Ltd.), was used instead of the aforementioned transglutaminase, thereby obtaining another test solution having the same concentration of 3 U/ml (Comparative example).

Blank test was carried out using the aforementioned HEPES buffer alone as a test solution (Control example).

(c) Wound provision:

Each rat under anesthesia was sheared (7 cm×7 cm) at its dorsal portion, using a pair of hair clippers, and the sheared part was disinfected with a "Hibitane" solution, from which part a piece of the skin was subsequently excised in a size of about 5 cm square using a scalpel.

was carried out only on the day of the wound provision, gauzes being exchanged on the subsequent days.

On the day following the administration, each rat was checked for the presence of pains and the degree of bleeding.

On the next day but one, namely 2 days after the administration, one rat of each group was sacrificed to collect its wound portion, which was subsequently fixed with formalin and made into a tissue specimen to carry out a histopathological inspection.

(e) Results:

Results of the observation with regard to the presence of pains are shown in Table 2 below.

TABLE 2

| | Degree of pains | | |
|---|---|---|---|
| Group | − | ± | + |
| I (Inventive) | 2 animals | 3 animals | 0 animal |
| II (Comparative) | 0 | 1 | 4 |
| III (Control) | 0 | 0 | 5 |

−: no complaint of pain
±: slight complaint of pain
+: complaint of pain

Results of the observation with regard to the degree of bleeding are shown in Table 3 below.

TABLE 3

| Group | Degree of bleeding | | | findings |
|---|---|---|---|---|
| | − | ± | + | |
| I (Inventive) | 0 animal | 5 animals | 0 animal | bleeding found only on wound periphery |
| II (Comparative) | 0 | 2 | 3 | bleeding found only on wound periphery |
| III (Control) | 0 | 2 | 3 | bleeding found both on entire granulating wound and wound periphery |

−: no bleeding
±: slight bleeding
+: bleeding

Results of the histopathological inspection are shown in Table 4 below.

TABLE 4

| Group | Findings |
|---|---|
| III (Control) | Hydropic degeneration of subcutaneous tissue, internal bleeding, infiltration of neutrophil and slight infiltration of macrophage and fibroblast were observed. |
| I (Inventive) | Hydropic degeneration, internal bleeding and infiltration of neutrophil were slighter than those of the control group, and infiltration degrees of macrophage and fibroblast were almost the same as those of the control group. As a remarkable point, generation of a membrane-like layer was observed on the wound surface. |
| II (Comparative) | Infiltration degrees of macrophage and fibroblast were almost the same as those of the control group. Hydropic degeneration of subcutaneous tissue was slighter than that of the control group, but inter-muscular internal bleeding and hydropic degeneration were more serious in comparison with those of the control group. Additionally, generation of muscle cell necrosis and considerably strong infiltration of neutrophil were observed. |

As can be seen from the above results, transglutaminase is superior to blood coagulation factor XIII as a hemostatic agent from the view point of pain, bleeding, histopathology and the like, which may be attributable to the following reasons. That is, since the hemostatic function of the blood coagulation factor is effected within the blood, its administration by means of wound surface application and the like does not result in the formation of a membrane-like layer, thus failing to effect its hemostatic function, while, in the case of transglutaminase, this enzyme seems to form a membrane-like layer by cross-linking effusion protein, cell surface protein and blood protein thereby exerting a notable hemostatic function.

Industrial Applicability

Wound healing agents, especially an excellent wound healing agent with which cicatricial contracture prevention, wound protection or coating and blood stanching can be made simply and easily, have been newly provided by the present invention.

We claim:

1. A wound healing composition consisting essentially of a wound healing effective amount of a calcium-independent transglutaminase isolated from a bacteria belonging to the genus Streptoverticillium and a pharmaceutically acceptable carrier.

2. The composition of claim 1, wherein said transglutaminase is present in an amount of from 0.5 to 500 U/g.

3. The composition of claim 2, wherein said composition is in contact with a wound.

4. The composition of claim 2, wherein said composition is in contact with a wound dressing.

5. The composition as claimed in claim 4, wherein said wound dressing is gauze.

6. The composition of claim 1, wherein said composition is in contact with a wound.

7. The composition of claim 1, wherein said composition is in contact with a wound dressing.

8. The composition as claimed in claim 7, wherein said wound dressing is gauze.

* * * * *

UNITED STATES PATENT AND TRADEMARK OFFICE
CERTIFICATE OF CORRECTION

PATENT NO. : 5,525,335
DATED : June 11, 1996
INVENTOR(S) : Kitahara et al.

It is certified that error appears in the above-identified patent and that said Letters Patent is hereby corrected as shown below:

Column 4, line 5, "Microbial transglutaminase"

should read

--Microbial *Streptoverticillium* transglutaminase--

Signed and Sealed this

Twenty-seventh Day of May, 1997

Attest:

BRUCE LEHMAN

*Attesting Officer*     *Commissioner of Patents and Trademarks*